(12) United States Patent
Kim

(10) Patent No.: US 7,758,743 B2
(45) Date of Patent: Jul. 20, 2010

(54) ELECTROCHEMICAL CORROSION POTENTIAL SENSOR AND METHOD OF MAKING

(75) Inventor: Young Jin Kim, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 554 days.

(21) Appl. No.: 11/654,263

(22) Filed: Jan. 17, 2007

(65) Prior Publication Data

US 2008/0169205 A1    Jul. 17, 2008

(51) Int. Cl.
*G01N 17/04* (2006.01)
(52) U.S. Cl. .................. 205/775.5; 204/404
(58) Field of Classification Search .......... 204/400, 204/404; 205/775, 775.5; 324/71.2, 693, 324/700
See application file for complete search history.

(56) References Cited

U.S. PATENT DOCUMENTS

| | | | | |
|---|---|---|---|---|
| 5,085,742 | A * | 2/1992 | Dollard et al. | 205/188 |
| 5,332,449 | A * | 7/1994 | Verstreken et al. | 136/234 |
| 6,357,284 | B1 | 3/2002 | Kim et al. | 73/86 |
| 6,411,667 | B2 | 6/2002 | Kim et al. | 376/305 |
| 6,610,185 | B2 | 8/2003 | Kim et al. | 204/404 |
| 2004/0066874 | A1 * | 4/2004 | Kim et al. | 376/305 |

* cited by examiner

*Primary Examiner*—Alex Noguerola
(74) *Attorney, Agent, or Firm*—Ann M. Agosti

(57) ABSTRACT

A sensor for measuring electrochemical corrosion potential includes an electrical conductor, a metal-oxide layer disposed on the electrical conductor, and a zirconia-containing layer disposed on the metal-oxide layer, wherein the zirconia-containing layer is disposed about the electrical conductor using thermal spraying, wire arc, ion plasma cathodic arc deposition, laser ablation, chemical vapor deposition, physical vapor deposition, electroplating, electroless plating, electrochemical oxidation, chemical oxidation, electrophoretic deposition, or radio-frequency sputtering.

17 Claims, 2 Drawing Sheets

ELECTROCHEMICAL CORROSION POTENTIAL SENSOR AND METHOD OF MAKING

BACKGROUND OF THE INVENTION

The present disclosure generally relates to electrochemical sensors. More particularly, it relates to sensors for determining the electrochemical corrosion potential (ECP) of metal components in liquids at high temperatures and pressures, as well as to methods of using the sensors.

Many areas of industry, such as the power generation industry, employ metal structural components that are exposed to liquids at high temperatures and pressures. Examples of systems in which equipment is designed for such exposure include nuclear reactors, including the boiling water and pressurized water type reactors, fossil fuel systems, and geothermal systems. In a boiling water nuclear reactor, for example, water and steam are channeled through various conduits formed of iron (Fe) and nickel (Ni) based alloys. Normal water chemistry conditions produced by radiolysis in-core, include highly oxidizing species, such as oxygen and hydrogen peroxide, which may lead to high electrochemical corrosion potential (ECP) and, eventually, intergranular stress corrosion cracking of the stainless steel.

Intergranular stress corrosion cracking can be mitigated by lowering the concentrations of oxidizing species in the reactor water, which results in low ECPs. The hydrogen is added to the feed water of the reactor to reduce the dissolved oxidant concentration and lower the ECP below a specific value at which intergranular stress corrosion cracking susceptibility is significantly reduced. When hydrogen water chemistry is practiced in a boiling water reactor, the electrochemical corrosion potential of the stainless steel components decreases from a positive value, generally about 0.050 to about 0.200 volts (V), based on a standard hydrogen electrode (SHE) as a reference, under normal water chemistry to a value of less than about −0.230 V (SHE). There is considerable evidence that when the electrochemical corrosion potential is below this negative value, intergranular stress corrosion cracking of stainless steel can be mitigated and the intergranular stress corrosion cracking initiation can be prevented.

Thus, considerable efforts have been made in the past decade to develop reliable electrochemical corrosion potential sensors to be used as reference electrodes to determine the electrochemical corrosion potential of operating surfaces. These sensors have been used in boiling water reactors worldwide, which has enabled the determination of the optimum feedwater hydrogen injection rate required to achieve electrochemical corrosion potential of reactor internal surfaces and piping below the desired negative value.

Various forms of ECP sensors are used for measuring ECPs in nuclear reactors and other systems. However, these sensors are subject to different problems that limit their useful lives. For a nuclear reactor, for example, the useful life of a sensor should cover the duration of at least a single fuel cycle, which is in the range of about 18 months to about 24 months in the United States. Experience in actual nuclear reactors has demonstrated sensor failure in a shorter duration due to various causes. An ECP sensor experiences a severe operating environment in view of the high temperature of water, well exceeding 280 degrees Celsius (° C.), and relatively high flow rates thereof, up to and exceeding several meters per second (m/s).

One type of ECP sensor includes a ceramic probe in the form of a zirconia tube brazed to a metal alloy tube. Since the ceramic probe and metal tube have different coefficients of thermal expansion, they are subject to thermal shock during high temperature operation which can lead to cracking of the braze joint. The braze material is also subject to corrosion during operation. Both problems limit the useful life of the sensor, since failure of the brazed joint causes water leakage inside the sensor and failure thereof.

Accordingly, a continual need exists for improved ECP sensors with increased operating lifetimes.

BRIEF SUMMARY

Disclosed herein is an electrochemical corrosion potential (ECP) sensor and a method of using an ECP sensor. In one embodiment, a sensor for measuring electrochemical corrosion potential includes an electrical conductor, a metal-oxide layer disposed on the electrical conductor, and a zirconia-containing layer disposed on the metal-oxide layer.

A method of using a electrochemical corrosion potential sensor in a reactor circuit, the method comprises coupling a reference electrode to a measurement electrode through a potentiometer, wherein the reference electrode comprises an electrical conductor, a metal-oxide layer disposed on the electrical conductor, and a zirconia-containing layer disposed on the metal-oxide layer, and disposing the reference electrode and the measurement electrode in reactor water.

A measurement system comprises a reference electrode comprising an electrochemical corrosion potential sensor, wherein the electrochemical corrosion potential sensor comprises an electrical conductor, a metal-oxide layer disposed on the electrical conductor, and a zirconia-containing layer disposed on the metal-oxide layer, a measurement electrode, and a potentiometer in operative communication with the reference electrode and the measurement electrode.

The above described and other features are exemplified by the following Figures and detailed description.

BRIEF DESCRIPTION OF THE DRAWINGS

Referring now to the drawings wherein like elements are numbered alike in several Figures.

DETAILED DESCRIPTION

Disclosed herein is an electrochemical corrosion potential (ECP) sensor and a method of using the sensor to measure the electrochemical corrosion potential of surfaces exposed to water at temperatures of 200 degrees Celsius (° C.) or higher, such as in fossil fuel, geothermal, and nuclear power plants. In one example, the disclosed ECP sensor may be designed for use in nuclear reactors. In contrast to the prior art, the ECP sensor disclosed herein employs a metal oxide coating disposed directly on an electrical conductor. By coating the metal oxide layer and a zirconia-containing layer directly to the electrical conductor, the need for a ceramic tube and a ceramic-to-metal braze for fixing the ceramic tube to the metal alloy tube is eliminated. Two of the most common modes of failure in currently existing ECP sensors are consequently removed. As such, the disclosed ECP sensor has a longer operating lifetime of at least about one fuel cycle, which is expected to be about 18 months or longer. Moreover, the sensor as disclosed herein has thermodynamic, physical, and chemical stability in high temperature water as well as stability in a wide range of pH environments, which further improves the operating lifetime of the ECP sensor. As used herein, the term "fuel cycle" refers to the progression of nuclear fuel through a series of differing stages. It comprises steps in the so-called "front end", which include the preparation of the fuel, the service period in which the fuel is used during reactor operation, and steps in the so-called "back end", which are necessary to safely manage, contain, and either reprocess or dispose of spent nuclear fuel.

Figure 1:
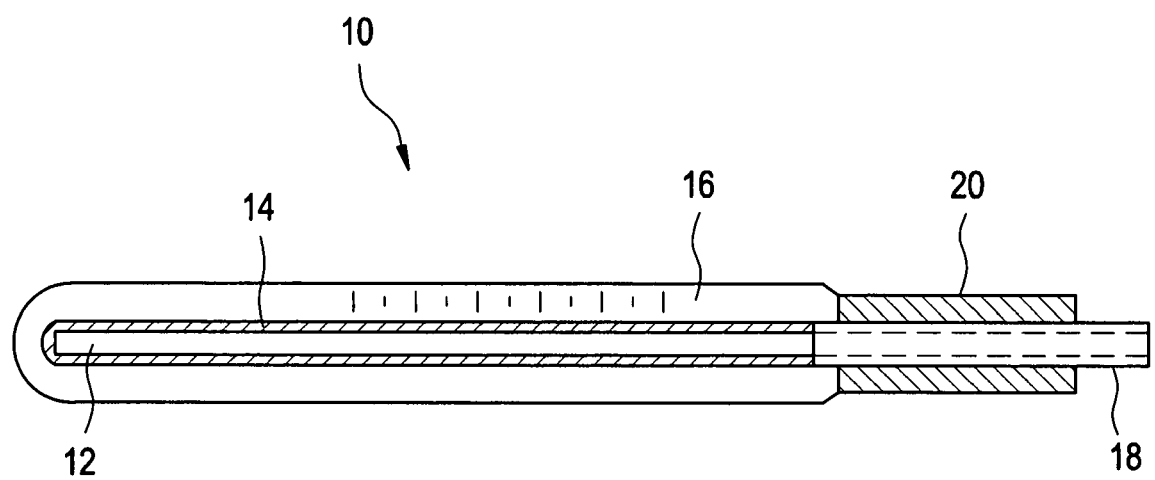
FIG. 1 is a cross-sectional schematic representation of an electrochemical corrosion potential sensor.

Referring now to FIG. 1, an ECP sensor 10 includes an electrical conductor 12, and a metal oxide layer 14 and a zirconia-containing layer 16 disposed on the electrical conductor 12. In a particular embodiment, a central conducting cable 18 may optionally be joined to the electrical conductor 12 for electrical communication therewith by a suitable joining method such as spot welding. An insulating sleeve 20 may be disposed about the central conducting cable 18 and in physical communication with the metal oxide layer 14. The insulating sleeve 20 may comprise a suitable mineral oxide or suitable polymer such as, but not intended to be limited to, polytetrafluoroethylene and silicone. In an exemplary embodiment, the insulating sleeve 20 comprises a mineral oxide such as alumina, magnesia, zirconia, yttria, or a combination comprising at least one of the foregoing.

The electrical conductor 12 may comprise any metal suitable for conductivity of an electrical current, such as copper, titanium, tantalum, platinum, silver, nickel, tungsten, stainless steel, alloys, and the like. The electrical conductor 12 may have any suitable substrate shape. For example, the electrical conductor 12 may be cylindrical, square, hexagonal, and the like. In one embodiment, the electrical conductor 12 is specifically cylindrical, wherein the conductor is a metal wire, such as nickel or stainless steel wire. Likewise, the metal oxide layer 14 and/or the zirconia-containing layer 16 may also have any suitable shape. In one embodiment the metal oxide layer 14 and the zirconia-containing layer 16 have cylindrical shapes structured to at least substantially mirror the shape of the electrical conductor 12 on which the two layers are disposed. In another embodiment, the two layers have shapes different than the shape of the electrical conductor 12. As will be appreciated by those skilled in the art, the specific shapes of the sensor 10 components are not intended to be limited.

The metal-oxide layer 14 coats the surface of the electrical conductor 12 and comprises a metal oxide. The selection of a suitable metal oxide layer material considers a variety of factors, particularly in those embodiments in which the ECP sensor 10 is designed for use in nuclear reactors, such as boiling water reactors (BWR), pressurized water reactors (PWR), and pressurized heavy water reactors, such as Canadian Deuterium-Uranium (CANDU) reactors. Factors to consider include, for example, cost, corrosion resistance, potential to form radioactive isotopes during service exposure, stability in high temperature, and stability in a wide range of pH environments. Suitable metal oxide layer materials include, but are not intended to be limited to, copper oxide, tungsten oxide, tantalum oxide, platinum oxide, silver oxide, nickel oxide, iron oxide, titanium oxide, and the like. In one embodiment, the material used to form metal-oxide layer 14 comprises the oxide of the metal employed in the electrical conductor 12. For example, where an embodiment employs an electrical conductor comprising copper, the metal-oxide layer would comprise copper oxide. Alternatively, in another embodiment, where the electrical conductor 12 comprises stainless steel, the metal-oxide layer 14 may comprise iron oxide.

The zirconia-containing layer 16 comprises the outer surface of the ECP sensor 10 and contains a form or variant of zirconia. Specific materials that can be used in the zirconia-containing layer 16 include zirconia ($ZrO_2$), stabilized zirconias, such as, magnesia stabilized zirconia (MSZ), yttria stabilized zirconia (YSZ), calcia stabilized zirconia, scandia stabilized zirconia, combinations comprising at least one of the foregoing, e.g., scandia-yttria stabilized zirconia, and the like. The zirconia-containing layer 16 may be deposited onto the metal oxide coating layer 14 by any suitable coating or deposition techniques. Such techniques may include, but are not limited to, thermal spraying (e.g., plasma spraying, high-velocity oxy-fuel spraying, high-velocity air-fuel spraying, and the like), chemical vapor deposition (CVD), physical vapor deposition (PVD), wire-arc, ion plasma cathodic arc deposition, laser ablation, electroplating, electroless plating, electrochemical deposition, chemical oxidation, electrophoretic coating, and radiofrequency (RF) sputtering.

The metal-oxide layer 14 may be generated through oxidation of the metal of the electrical conductor 12 during deposition of the zirconia-containing layer 16 onto the electrical conductor. In addition, or in the alternative, the metal-oxide layer 14 may be deposited on the conductor 12 via any of the processes listed above. For example, if the electrical conductor 12 is stainless steel, the stainless steel may oxidize to form iron oxide as the zirconia-containing layer 16 is being thermally sprayed onto the stainless steel conductor 12. However, it may be possible to deposit a metal oxide layer (iron oxide or other metal oxide) before the zirconia-containing layer 16 is deposited onto the stainless steel conductor. The thickness of the metal-oxide layer 14, which is generally about 10 nanometers (nm) to about 100 micrometers ($\mu$m), depends in part upon which method of creating the metal-oxide layer 14 is used. If the metal-oxide layer 14 is generated naturally, i.e., formed during deposition of the zirconia-containing layer 16, the metal-oxide layer thickness can be about 5 $\mu$m to about 10 $\mu$m.

Similarly, the thickness of the zirconia-containing layer 16, which is generally about 1 micrometer to about 3 millimeters (mm), depends in part upon the particular process employed to deposit the layer. For example, a plasma-sprayed coating comprises a level of porosity that is higher than that of coatings deposited by the other processes identified above, such as CVD, PVD, and the like. As a result, coatings deposited by plasma spray are often deposited at a higher thickness; for example, a thickness of about 0.03 mm to about 3 mm, to ensure that the coating exhibits desired levels of protection. The advantageously high-porosity coatings provided by processes exemplified by chemical vapor deposition and electroplating allow for effective protection of the electrical conductor 12 by layers as thin as about 1 micrometer ($\mu$m) for certain embodiments. The aggressiveness of the environment in which the ECP sensor 10 is employed also has a part in determining desirable thickness for the zirconia-containing layer 16. Environmental concerns may include, but are not limited to, impurity levels, temperature, flow rate, radiation level, and oxidizing conditions. The desired thickness of the zirconia-containing layer 16 is generally increased for more aggressive exposure conditions.

Figure 2:
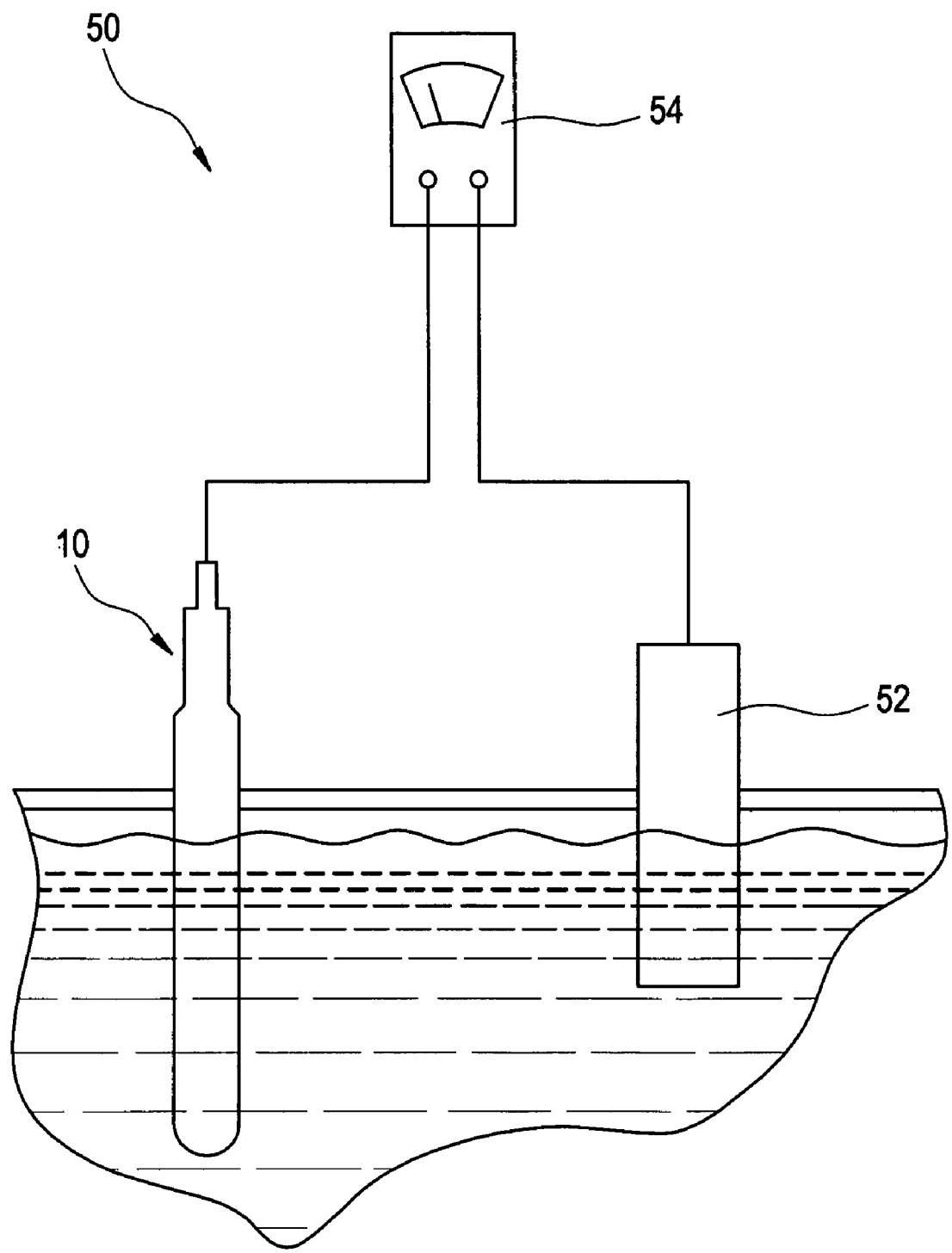
FIG. 2 is a schematic illustration of an electrochemical corrosion potential sensor in use in a reactor circuit.

Turning now to FIG. 2, an embodiment of the ECP sensor 10 in use is illustrated as part of an exemplary nuclear reactor measurement system 50. The ECP sensor 10 functions as a reference electrode, and is coupled to a measurement electrode 52 situated elsewhere in the reactor circuit 50 through a potentiometer 54. Suitable materials for the measurement electrode 52 are known to those skilled in the art, and may include any metals, e.g., metal alloys, platinum, silver, gold, tantalum, rhodium, and the like. In an exemplary embodiment, the measurement electrode 52 is stainless steel or platinum. When the reactor water conditions such as temperature and pH are known, the potentiometer 54 may be read and the readings used to calculate the electrochemical corrosion potential. The reference potential of the sensor 10 varies depending upon the particular pH and temperature of the environment.

Other embodiments of the ECP sensor disclosed herein provide a method of using a sensor to measure electrochemical corrosion potential. The method includes coupling a reference electrode to a measurement electrode through a potentiometer, wherein the reference electrode comprises an electrical conductor and a metal oxide coating layer disposed on the electrical conductor, and disposing the reference electrode and the measurement electrode in reactor. When the reactor water temperature and pH are known, the potentiometer can be read to calculate the ECP value based on the ECP sensor as a reference.

Advantageously, the ECP sensor disclosed herein has a longer useful life under nuclear reactor operating conditions than existing sensors. The individual lifetimes of currently available sensors are as short as a few weeks and as long as one fuel cycle. Such short lifetimes are a result of failure on the ceramic tube-alloy interfaces and corrosion of the braze materials in prior art sensors. By removing the need for a ceramic tube, the disclosed sensor eliminates the degradation of the ceramic/alloy bond. Moreover, the disclosed ECP sensor eliminates the need for a metal/metal-oxide powder packed within the ceramic tube. Even further, the disclosed sensor also employs a brazeless bond between the electrical conductor and the metal oxide coating layer, thereby eliminating the possibility of corrosion of a braze joint. Removal of these two common modes of failure in existing sensors results in the disclosed ECP sensor, which has an improved use life of expected to be at least about one fuel cycle or greater than about 18 months.

While the invention has been described with reference to an exemplary embodiment, it will be understood by those skilled in the art that various changes maybe be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A sensor for measuring electrochemical corrosion potential comprising:
   an electrical conductor comprising a metal;
   a metal-oxide coating layer disposed on the electrical conductor comprising an oxide of the metal of the electrical conductor;
   a zirconia-containing layer disposed on the metal-oxide layer; and not comprising a metal/metal oxide powder packing.

2. The sensor of claim 1, wherein the metal oxide coating layer has an operating lifetime of at least one fuel cycle of a nuclear reactor.

3. The sensor of claim 1, wherein the electrical conductor comprises nickel, iron, copper, titanium, silver, platinum, tungsten, tantalum, an alloy comprising at least one of the foregoing, or a combination comprising at least one of the foregoing.

4. The sensor of claim 3, wherein the alloy is stainless steel.

5. The sensor of claim 1, wherein the zirconia-containing layer comprises zirconia, magnesia stabilized zirconia, yttria stabilized zirconia, calcia stabilized zirconia, scandia stabilized zirconia, or a combination comprising at least one of the foregoing.

6. The sensor of claim 1, further comprising a central conducting cable coupled to the electrical conductor for electrical communication therewith.

7. The sensor of claim 6, further comprising an insulating sleeve disposed about the central conducting cable.

8. The sensor of claim 1, wherein the zirconia-containing layer has a thickness of about 1 micrometer to about 3 millimeters.

9. The sensor of claim 1, wherein the zirconia-containing layer is disposed about the electrical conductor using thermal spraying, wire arc, ion plasma cathodic arc deposition, laser ablation, chemical vapor deposition, physical vapor deposition, electroplating, electroless plating, electrochemical oxidation, chemical oxidation, electrophoretic deposition, or radio-frequency sputtering.

10. A method of using an electrochemical corrosion potential sensor in a reactor circuit, the method comprising:
    coupling a reference electrode to a measurement electrode through a potentiometer, wherein the reference electrode comprises an electrical conductor, a metal-oxide coating layer disposed on the electrical conductor, and a zirconia-containing layer disposed on the metal-oxide layer and does not comprise a metal/metal oxide powder packing; and
    disposing the reference electrode and the measurement electrode in reactor water.

11. The method of claim 10, wherein the reference electrode is structured to have an operating life of at least one fuel cycle of a nuclear reactor.

12. The method of claim 10, wherein the electrical conductor comprises nickel, iron, copper, titanium, silver, platinum, tungsten, tantalum, stainless steel, an alloy comprising at least one of the foregoing, or a combination comprising at least one of the foregoing.

13. The method of claim 10, wherein the zirconia-containing layer comprises zirconia, magnesia stabilized zirconia, yttria stabilized zirconia, calcia stabilized zirconia, scandia stabilized zirconia, or a combination comprising at least one of the foregoing.

14. The method of claim 10, wherein the zirconia-containing layer has a thickness of about 1 micrometer to about 3 millimeters.

15. The method of claim 10, wherein the zirconia-containing layer is disposed on the metal-oxide layer by a process selected from the group comprising thermal spraying, wire arc, ion plasma cathodic arc deposition, laser ablation, chemical vapor deposition, physical vapor deposition, electroplating, electroless plating, electrochemical oxidation, chemical oxidation, electrophoretic deposition, radio-frequency sputtering, or a combination comprising at least one of the foregoing.

16. A measurement system comprising:
    a reference electrode comprising an electrochemical corrosion potential sensor, wherein the electrochemical corrosion potential sensor comprises an electrical conductor comprising a metal, a metal-oxide coating layer comprising an oxide of the electrical conductor disposed on the electrical conductor, and a zirconia-containing layer disposed on the metal-oxide layer and does not comprise a metal/metal oxide powder packing;
    a measurement electrode; and
    a potentiometer in operative communication with the reference electrode and the measurement electrode.

17. The system of claim 16, wherein the zirconia-containing has an operating lifetime of at least one fuel cycle of a nuclear reactor.

* * * * *